(12) United States Patent
Oral et al.

(10) Patent No.: US 9,037,223 B2
(45) Date of Patent: May 19, 2015

(54) ATRIAL FIBRILLATION CLASSIFICATION USING POWER MEASUREMENT

(71) Applicant: THE REGENTS OF THE UNIVERSITY OF MICHIGAN, Ann Arbor, MI (US)

(72) Inventors: Hakan Oral, Ann Arbor, MI (US); Omer Berenfeld, Ann Arbor, MI (US); Grant Kruger, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 13/738,626

(22) Filed: Jan. 10, 2013

(65) Prior Publication Data

US 2013/0197380 A1    Aug. 1, 2013

Related U.S. Application Data

(60) Provisional application No. 61/584,954, filed on Jan. 10, 2012.

(51) Int. Cl.
*A61B 5/0452* (2006.01)
*A61B 5/046* (2006.01)
*A61N 1/39* (2006.01)
(Continued)

(52) U.S. Cl.
CPC .............. *A61B 5/0452* (2013.01); *A61B 5/046* (2013.01); *A61N 1/3956* (2013.01); *A61B 5/7264* (2013.01); *A61B 5/04014* (2013.01); *A61B 5/04017* (2013.01); *A61B 5/0428* (2013.01); *A61B 5/7257* (2013.01)

(58) Field of Classification Search
CPC ............................ A61N 5/046; A61N 5/0464
USPC .................................................. 600/515, 518
See application file for complete search history.

(56) References Cited

U.S. PATENT DOCUMENTS 5,077,667 A    12/1991    Brown et al.
5,295,484 A     3/1994    Marcus et al.
(Continued)

FOREIGN PATENT DOCUMENTS

EP    1038498 A2    9/2000
EP    1595575 A2   11/2005
(Continued)

OTHER PUBLICATIONS

Atienza, et al., "Activation of inward rectifier potassium channels accelerates atrial fibrillation in humans: evidence for a reentrant mechanism," Circulation 1 14(23):2434-42 (2006).
(Continued)

*Primary Examiner* — Joseph Dietrich
(74) *Attorney, Agent, or Firm* — Marshall, Gerstein & Borun LLP

(57) ABSTRACT

An atrial fibrillation classification system collects celectro-cardiogram signals and converts them to a frequency, time, or phase domain representation for analysis. An evaluation stage extracts energy density profile over a range of frequencies, time intervals, or phases, which is then summed and normalized to form dispersion metrics. The system then analyzes the dispersion metrics, in their respective domains, to determine whether a patient is experiencing an arrhythmia and then to classify the type of arrhythmia being experienced.

32 Claims, 12 Drawing Sheets

(51) Int. Cl.
*A61B 5/00* (2006.01)
*A61B 5/04* (2006.01)
*A61B 5/0428* (2006.01)

(56) References Cited

U.S. PATENT DOCUMENTS

| | | | |
|---|---|---|---|
| 5,772,604 | A | 6/1998 | Langberg et al. |
| 5,776,168 | A | 7/1998 | Gunderson |
| 5,792,189 | A | 8/1998 | Gray et al. |
| 5,814,079 | A | 9/1998 | Kieval |
| 6,006,133 | A | 12/1999 | Lessar et al. |
| 6,009,348 | A | 12/1999 | Rorvick et al. |
| 6,263,238 | B1 | 7/2001 | Brewer et al. |
| 6,295,475 | B1 | 9/2001 | Morgan |
| 6,337,995 | B1 | 1/2002 | Mower |
| 6,597,943 | B2 | 7/2003 | Taha et al. |
| 6,654,639 | B1 | 11/2003 | Lu |
| 6,748,274 | B2 | 6/2004 | Levine et al. |
| 6,921,295 | B2 | 7/2005 | Sommer et al. |
| 6,931,280 | B1 | 8/2005 | Yang |
| 6,959,214 | B2 | 10/2005 | Pape et al. |
| 6,968,237 | B2 | 11/2005 | Doan et al. |
| 7,117,030 | B2 | 10/2006 | Berenfeld et al. |
| 7,123,954 | B2 | 10/2006 | Narayan et al. |
| 7,142,919 | B2 | 11/2006 | Hine et al. |
| 7,174,210 | B1 | 2/2007 | Levine |
| 7,181,272 | B2 | 2/2007 | Struble et al. |
| 7,233,822 | B2 | 6/2007 | Hettrick et al. |
| 7,236,821 | B2 | 6/2007 | Cates et al. |
| 7,269,457 | B2 | 9/2007 | Shafer et al. |
| 7,302,294 | B2 | 11/2007 | Kamath et al. |
| 7,383,085 | B2 | 6/2008 | Olson |
| 7,499,750 | B2 | 3/2009 | Haefner et al. |
| 7,505,810 | B2 | 3/2009 | Harlev et al. |
| 7,509,170 | B2 | 3/2009 | Zhang et al. |
| 7,515,954 | B2 | 4/2009 | Harlev et al. |
| 7,610,090 | B1 | 10/2009 | Hofstadter et al. |
| 7,630,764 | B2 | 12/2009 | Ding et al. |
| 7,643,879 | B2 | 1/2010 | Shuros et al. |
| 7,650,182 | B2 | 1/2010 | Kim et al. |
| 7,676,272 | B2 | 3/2010 | Lang |
| 7,689,280 | B1 | 3/2010 | Kroll et al. |
| 7,702,390 | B1 | 4/2010 | Min |
| 7,751,888 | B1 | 7/2010 | Schecter |
| 7,819,862 | B2 | 10/2010 | Pachon Mateos et al. |
| 2005/0245974 | A1 | 11/2005 | Sherman |
| 2005/0288725 | A1 | 12/2005 | Hettrick et al. |
| 2006/0025824 | A1* | 2/2006 | Freeman et al. .......... 607/5 |
| 2007/0021679 | A1 | 1/2007 | Narayan et al. |
| 2008/0167567 | A1 | 7/2008 | Bashour et al. |
| 2009/0292180 | A1 | 11/2009 | Mirow |
| 2011/0060327 | A1 | 3/2011 | Pachon Mateos et al. |
| 2011/0098699 | A1 | 4/2011 | Pachon Mateos et al. |
| 2011/0301586 | A2 | 12/2011 | Pachon Mateos et al. |

FOREIGN PATENT DOCUMENTS

| | | |
|---|---|---|
| WO | WO-96/25093 A1 | 8/1996 |
| WO | WO-2005/115232 A1 | 12/2005 |
| WO | WO-2006/004700 A1 | 1/2006 |
| WO | WO-2007/103744 A2 | 9/2007 |

OTHER PUBLICATIONS

Atienza, et al., "Real-time Dominant Frequency Mapping and Ablation of Dominant-Frequency Sites in Atrial Fibrillation with Left-to-Right Frequency Gradients Predicts Long-Term Maintenance of Sinus Rhythm," Heart Rhythm 6(1):33-40 (2009).

Berenfeld "Complex Fractionated Atrial Electrograms: Is This the Beast to Tame in Atrial Fibrillation?," Circ Arrhythm Electrophysiol. 4(4):426-8 (2011).

Berenfeld, "Quantifying activation frequency in atrial fibrillation to establish underlying mechanisms and ablation guidance," Heart Rhythm 4(9):1225-34 (2007).

Berenfeld, et al., "Spatially distributed dominant excitation frequencies reveal hidden organization in atrial fibrillation in the Langendorff-perfused sheep heart," J Cardiovasc. Electrophysiol, 11(8):869-79 (2000).

Berenfeld, et al., "Time and Frequency Domains Analyses of Atrial Fibrillation Activation Rate: The Optical Mapping Reference," Heart Rhythm 8(11):1758-1765 (2011).

Chan, et al., "Cost-Effectiveness of Radiofrequency Catheter Ablation for Atrial Fibrillation," J Am Coll Cardiol. 47(12):2513-20 (2006).

Chang, et al. "Time- and Frequency-Domain Characteristics of Atrial Electrograms During Sinus Rhythm and Atrial Fibrillation," J. Cardiovasc. Electrophysiol. 22(8):851-7 (2011).

Daubert, et al. "Inappropriate Implantable Cardioverter-Defibrillator Shocks in MADIT II: Frequency, Mechanisms, Predictors, and Survival Impact," J. Am. Coll Cardiol 51(14):1357-65 (2008).

International Search Report & Written Opinion from PCT/US2013/021017 dated Aug. 6, 2013.

Jalife, et al., "Mother Rotors and Fibrillatory Conduction: a Mechanism of Atrial Fibrillation," Cardiovasc Res 54(2):204-16 (2002).

Lemola, et al., "Effects of Two Different Catheter Ablation Techniques on Spectral Characteristics of Atrial Fibrillation," J Am Coll Cardiol 18;48(2):340-8 (2006).

Oral, et al., "Risk of Thromboembolic Events After Percutaneous Left Atrial Radiofrequency Ablation of Atrial Fibrillation," Circulation 1 14(8):759-65 (2006).

Price, et al., "Time-Course of Dominant Frequency of Atrial Fibrillation in a Long Term in vivo Sheep Model." Heart Rhythm 8(5S):5470 (2011).

Sanders, et al., "Spectral Analysis Identifies Sites of High-Frequency Activity Maintaining Atrial Fibrillation in Humans," Circulation 112:789-97 (2005).

Seiler, "Atrial fibrillation in congestive heart failure," Cardiol Rev 18(1):38-50 (2010).

Yoshida, et al. "Relationship between the spectral characteristics of atrial fibrillation and atrial tachycardias that occur after catheter ablation of atrial fibrillation," Heart Rhythm 6(1):11-7 (2009).

Yoshida, et al., "Left atrial volume and dominant frequency of atrial fibrillation in patients undergoing catheter ablation of persistent atrial fibrillation," J. Interv Card Electrophysiol (2011).

International Preliminary Report on Patentability, corresponding International Application No. PCT/US2013/021017, dated Jul. 15, 2014.

* cited by examiner

ATRIAL FIBRILLATION CLASSIFICATION USING POWER MEASUREMENT

CROSS-REFERENCE TO RELATED APPLICATIONS

This application claims priority to U.S. Provisional Application No. 61/584,954, entitled "Atrial Fibrillation Classification Using Power Measurement," filed Jan. 10, 2012, which is hereby incorporated herein in their entirety.

FIELD OF TECHNOLOGY

The present disclosure relates generally to identifying heart rhythm state and, more particularly, to determining whether the heart rhythm is in a cardiac arrhythmia state, such as atrial fibrillation using a measured power value.

STATEMENT OF GOVERNMENTAL INTEREST

This invention was made with government support under HL039707 awarded by the National Institutes of Health. The Government has certain rights in the invention.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Atrial fibrillation is a form of cardiac arrhythmia where there is disorganized electrical conduction in the atria causing rapid uncoordinated depolarizations that result in ineffective pumping of blood into the ventricle and a lack of synchrony. During atrial fibrillation, the atrioventricular node receives electrical impulses from numerous locations throughout the atria instead of only from the sinus node. This overwhelms the atrioventricular node into producing an irregular and often rapid heartbeat. Due to the lack of organized contraction of the atria, blood may pool in the atria increasing the risk for blood clot formation. The major risk factors for atrial fibrillation include age, rheumatic heart disease, valvular heart disease, hypertension, diabetes, coronary artery disease, and thyrotoxicosis. Atrial fibrillation affects about 7% of the population over age 65. At present there are over 6 million patients affected with atrial fibrillation (AF) only in the US. It is estimated that by 2025 over 10 million patients will have atrial fibrillation. AF is the leading cause of strokes and is the most common arrhythmia leading to hospital admissions.

AF may be intermittent (paroxysmal) or persistent. It may be acute and terminate within a relatively short period of time, or it may be chronic and persist for years. AF may develop in patients with structurally normal hearts as well as in patients with associated comorbidities including structural heart disease. Based on the presence of clinical characteristics and comorbid conditions, patients with AF are at variable risk for stroke and other thromboembolic events. Therefore, based on the degree of risk of stroke, patients are treated either with antiplatelet or anticoagulant agents to reduce the risk of stroke. However these agents, on the other hand, do increase the risk of bleeding complications, including intracranial risk. Therefore, in patients with AF, risk of thromboembolic events, particularly stroke, compete against the risk of bleeding complications due to antiplatelet/anticoagulant agents. To optimize these competing risks, it is desirable to accurately identify when patients with a history of AF go into AF and how long they stay in AF.

AF treatment options are still evolving. In most patients restoring and maintaining sinus rhythm is preferred, as sinus rhythm is often associated with an improvement in quality of life, improvement in atrial and ventricular remodeling with an improvement in ejection fraction, possibly a reduction in the risk of thromboembolic events, and elimination of the need for anticoagulant therapy in most patients. Cardioversion attempts to restore sinus rhythm; yet even if successful acutely, AF may still recur as cardioversion does not eliminate the underlying mechanisms of AF. In addition, if there is a blood clot in the atria, cardioversion may cause the clot to leave the heart and travel to the brain (leading to stroke) or to some other part of the body.

One of the more recent procedures for treating cardiac arrhythmias is catheter ablation therapy. Physicians make use of specialized ablation catheters to gain access to interior regions of the body. Catheters with tip electrodes or other ablating devices are used to create ablation lesions that physiologically alter the ablated tissue without removal thereof, and thereby disrupt and/or block electrical pathways through the targeted tissue. In the treatment of cardiac arrhythmias, a specific area of cardiac tissue having aberrant electrically conductive pathways, such as atrial rotors, emitting or conducting erratic electrical impulses, is initially localized. A user (e.g., a physician) directs a catheter through a main vein or artery into the interior region of the heart that is to be treated. The ablating element or elements are next placed near the targeted cardiac tissue that is to be ablated, such as a pulmonary vein ostium or atrium.

While the available treatment methods provide various degrees of success, it is nonetheless difficult, at times, to determine the effectiveness of the treatment. Part of the difficulty arises because care professionals will typically rely, even partially, on the patient's perceived state of health to gauge effectiveness. Patients naturally have varying levels of perception; and moreover a patient may experience atrial fibrillation and not know it. This problem is in fact heightened after a medical procedure, when the patient has returned to normal life, and may begin experiencing atrial fibrillation while feeling as those their heart function is normal. Up to one-third of patients with AF do not appreciate or know that they are experiencing AF; and therefore, they do not know they are at heightened risk for stroke. It is, therefore, desirable to have an effective mechanism to measure atrial fibrillation that is cost effective and consistent in operation.

SUMMARY

In an embodiment, an apparatus for detecting arrhythmias within a body, the apparatus includes: an input stage to receive an electrocardiogram signal from a body connected thereto through a detection electrode input, wherein the input stage is a real-time dynamically adjustable signal transformation stage configured to condition the electrocardiogram signal; an analysis stage coupled to the input stage to receive the conditioned electrocardiogram signal from the input stage, wherein the analysis stage comprises, a transformation stage wherein a frequency and/or phase domain representation of the conditioned electrocardiogram signal is formed from the conditioned time-domain electrocardiogram signal, and an evaluation stage, wherein time, frequency and/or phase domain features related to the arrhythmias are extracted from the time, frequency and/or phase domain representation. Wherein one possible instantiation of the evaluation stage comprises a Spectral Dispersion Metric (SDM) evaluation stage configured to determine, for example, the dispersion of frequency energy over a predetermined range of frequencies relative to the frequency with the highest energy Spectral Frequency Dispersion Metric (SFDM), and/or Spectral Time Domain Dispersion metric (STDM) and/or Spectral Phase Domain Dispersion Metric (SPDM) representations and configured to normalize the energy to form a dispersion metric over the predetermined range of frequencies, time intervals and/or phases; and a classification stage coupled to the evaluation stage to receive the total normalized power and determine whether the body is experiencing the arrhythmias.

In accordance with another example an apparatus for detecting arrhythmias within a body, the apparatus includes: an input stage to receive an electrocardiogram signal from a body connected thereto through a detection electrode input, wherein the input stage is a real-time dynamically adjustable signal transformation stage configured to condition the electrocardiogram signal; an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to the arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the body is experiencing the arrhythmias.

In accordance with another example, an apparatus for detecting arrhythmias within a body, the apparatus includes: an input stage to receive an electrocardiogram signal from a body connected thereto through a detection electrode input, wherein the input stage is a real-time dynamically adjustable signal transformation stage configured to condition the electrocardiogram signal; an analysis stage coupled to the input stage to receive the conditioned electrocardiogram signal from the input stage, wherein the analysis stage comprises, a transformation stage wherein a time domain profile of the conditioned electrocardiogram signal is formed, and an evaluation stage configured to determine, over the time domain profile, at a plurality of predetermined time intervals and to determine the number of times a spectral time domain dispersion metric (STDM) is in one or more count ranges over the plurality of predetermined time intervals; and a classification stage coupled to the evaluation stage to receive the STDM and determine whether the body is experiencing the arrhythmias.

In accordance with another embodiment, a method of analyzing patient data, the patient data including electrocardiogram data, the method comprises: receiving, at an analysis machine, the electrocardiogram data from a database; identifying, at the analysis machine, target patient data from the database; processing, at the analysis machine, the target patient data and the electrocardiogram data; identifying, at the analysis machine, from the processed target patient data and the electrocardiogram data, diagnostic features using an adapting algorithm, wherein the diagnostic features represent correlations or patterns within the processed target patient data and the electrocardiogram data and wherein the diagnostic features correspond to a diagnosable condition of a patient; and assessing, at the analysis machine, the diagnostic features to determine the presence of the diagnosable condition for the patient.

BRIEF DESCRIPTION OF THE DRAWINGS

FIG. 2A is a plot of time domain electrocardiogram signals, taken over a sampling period, for a patient under normal sinus rhythm, while FIG. 2C is a plot of time domain electrocardiogram signals, taken over a sampling period, for a patient experiencing atrial fibrillation, while

DETAILED DESCRIPTION

Figure 1:
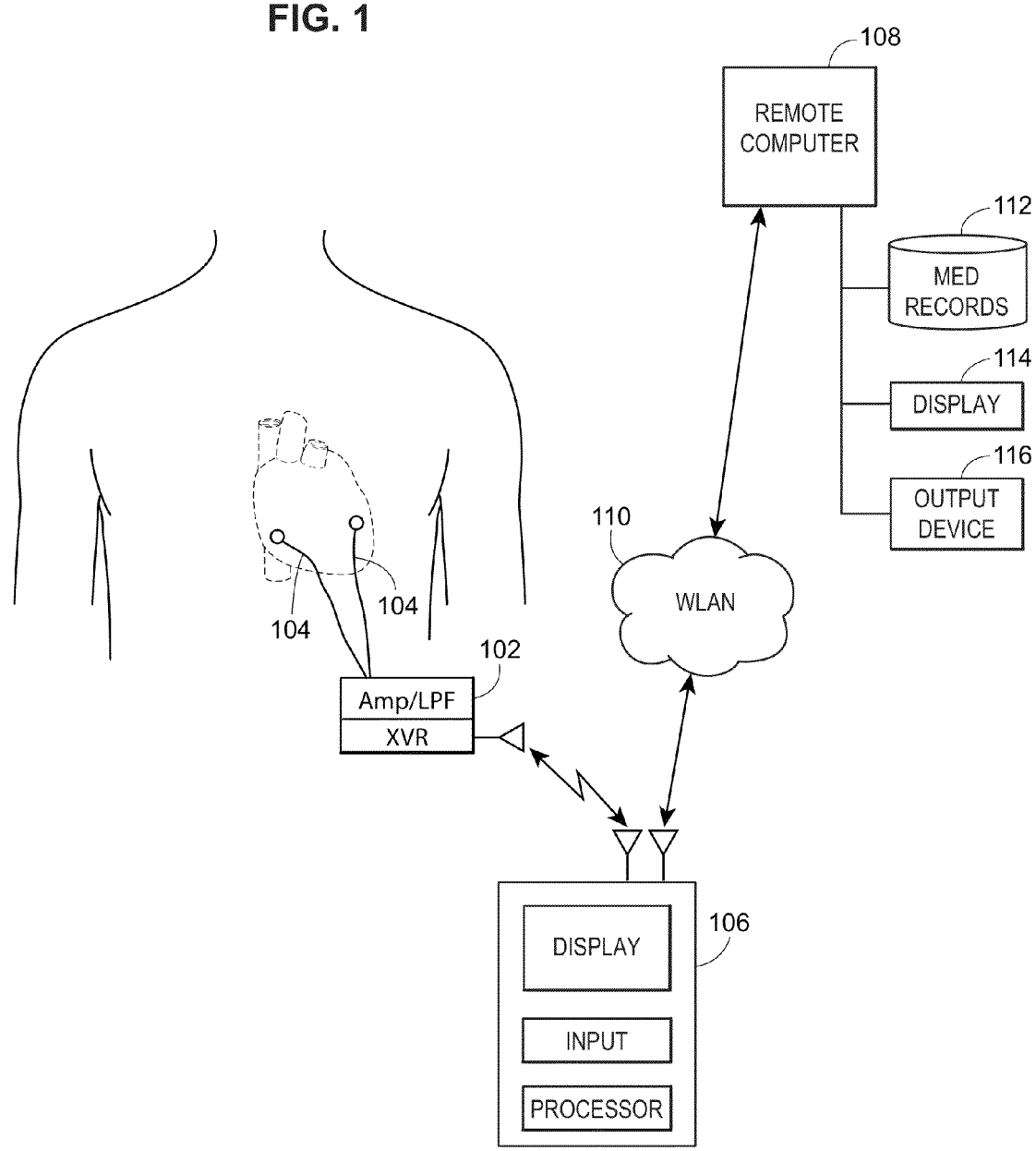
FIG. 1 is a diagram of a system for atrial fibrillation classification.

Generally, techniques herein describe methods and devices for the automated classification of a heart rhythm, across a spectrum from normal rhythm, called sinus rhythm, to cardiac arrhythmia, such as atrial fibrillation (AF). The techniques encompass measuring a metric of heart performance that is chosen to assess heart rhythm performance over a functional operation range. That metric is correlated to heart rhythm conditions in that different values are predetermined to indicate different rhythm conditions, from sinus rhythm to AF. More specifically, in various embodiments discussed below, the techniques involve determining a metric called the Spectral Frequency Dispersion Metric (SFDM), which is the sum of the spectrally distributed energy relative to the maximal energy over a set of specified frequencies and bands obtained from electrical recordings from the heart. The SFDM is, therefore, a metric related to the distribution of a heart performance metric (in this case a measured energy) across a specified functional operation range (in this case discrete or continuous frequency bands).

The performance metric(s) once determined (i.e. SFDM), is correlated to heart rhythm state for use in diagnostic classification. For example, a baselining procedure is performed to determine the optimal segmentation of clusters generated by the SFDM or transformations of the SFDM (i.e. mean, standard deviations, etc), each corresponding to a different heart rhythm state. In an example implementation, SFDM values within a first region are correlated as identifying sinus rhythm. SFDM values in a second region, exceeding predetermined critical values (i.e., the energy is widely distributed), are correlated to AF. While SFDM values in a third region, between the two, are correlated to an atrial flutter (AFL) condition. Multiple additional SFDM value ranges may be used to further parse the heart rhythm spectrum to identify cardiac arrhythmia states.

At the point of care or wherever patient assessment may be desired, the techniques may be implemented in a device having a form factor that is simple enough for patient use, allowing for user friendly operation, within or outside of a care facility. The techniques may be implemented in a single device or across multiple devices in a distributed fashion, and either way performing both SFDM measurement and heart rhythm classification, for easy identification by a patient or heath care professional. In some implementations, the device is a portable, stand-alone device that records electrical activity from the heart and then determines the presence of AF in patients, such as those that have already been diagnosed as being at a risk of developing intermittent episodes of arrhythmia. The device may be compact in size, e.g., hand-held, and with easy-to-apply electrodes to establish contact with the patient. Through these electrodes, electrical activity (and its vector) may be recorded from the patient, filtered, amplified and processed using unique embedded algorithms to detect the rhythm status.

The device may be designed to display both the measured electrical activity in real-time similar to an ECG monitor and the rhythm status, either to a separate monitor or to a display on the device itself. The simplest realization of the device may only employ indicator lights, or an audio/vibratory alert. The rhythm status may be displayable in both a common language manner (e.g., using phrases like "NORMAL", "ALARM", "ABNORMAL", "ATRIAL FIBRILLATION", "AF"), color-coded to alert the patient of the rhythm status or with the use of intuitive icons, or a combination thereof. In some examples, the techniques are implemented in a networked environment by which data measured from the device, whether displayed at the device or not, may be displayed at a remote system, such as at a healthcare facility (hospital, nurses station, doctors terminal, prescription system, hospital administration system). The device receiving real-time data may store that data in a structured, indexed, database for later retrieval by the device and for transmission to a central monitoring facility or other station, as mentioned herein, for example through a remote wireless network connection. The device may further include voice/sound feedback and/or tactile/vibratory feedback.

The present techniques may also allow for controlling operation of AF determination and assessment. For example, the device or other computer device networked therewith may provide a medical practitioner with an user input interface through which the practitioner may adjust operation of the device, including the sensitivity and specificity of AF assessments. In yet other examples, the present techniques may be used to store historic patient AF assessment data (e.g., ECG data) and perform data mining on that data, e.g., in an informatics-based manner to identify hard-to-notice, hidden, correlations of different time, frequency of phase patterns, for AF assessment and treatment protocol determination.

The techniques are able to offer numerous advantages and may be vitally important to determine the rhythm status in patients diagnosed with AF. The techniques will allow patients to know if they are in a normal sinus rhythm condition or in AF condition particularly during or after specific therapy applications, which may include pharmacological therapy with drugs or catheter or surgical based ablation therapies. During some therapy applications, patients are most at risk for stroke when they are experiencing AF. In such examples, an anticoagulant may be greatly helpful in reducing the risk of strokes due to blood clots. However, in other conditions, anticoagulants may increase the risk of bleeding particularly intracranial bleeding, which can cause serious consequences. Therefore, the present techniques provide a measured way for a patient to know if they are experiencing sinus rhythm or AF, so that the patient can know, on their own, whether or not to take an anticoagulant. Even outside of the therapeutic context, and more generally, patients may be experiencing AF and not be aware of it. If AF is untreated and is associated with rapid heart rates, this subsequently may impair the contractile function of the heart and may lead to a cardiomyopathy. With the present techniques, patients have a simplified method of identifying an AF condition.

FIG. 1 provides a schematic illustration of an atrial fibrillation classification system 100 having an electrode assembly 102 forming at least part of an input stage for the system 100. In the illustrated configuration, the electrode assembly 102 includes two sensing electrodes 104 that are to be mounted near a patient's heart, for example using a medical mounting tape. The electrodes 104 may be standard ECG electrodes, for example, capable of positioning at any desired location and reusable. The two electrode configuration, as shown, allows for using two input pre-amplification, amplification, and noise shaping circuitry, as desired. In another configuration, additional numbers of electrodes may be used for example as in a normal ECG measurement.

The electrode assembly 102 is coupled directly to the electrodes 104 in the illustrated embodiment and may include a signal amplifier, low pass filter, buffer, and/or other front end circuitry. In a wireless communication mode the electrode assembly 102 further includes an antenna and wireless transceiver stage coupled thereto. In an example, that wireless transceiver may be a Bluetooth transceiver stage for wireless communication with a handheld atrial fibrillation classification unit 106, also having an antenna and a Bluetooth transceiver stage. In some examples, the electrode assembly 102 is connected to the atrial fibrillation classification unit 106 through a direct, wired connection.

Figure 3:
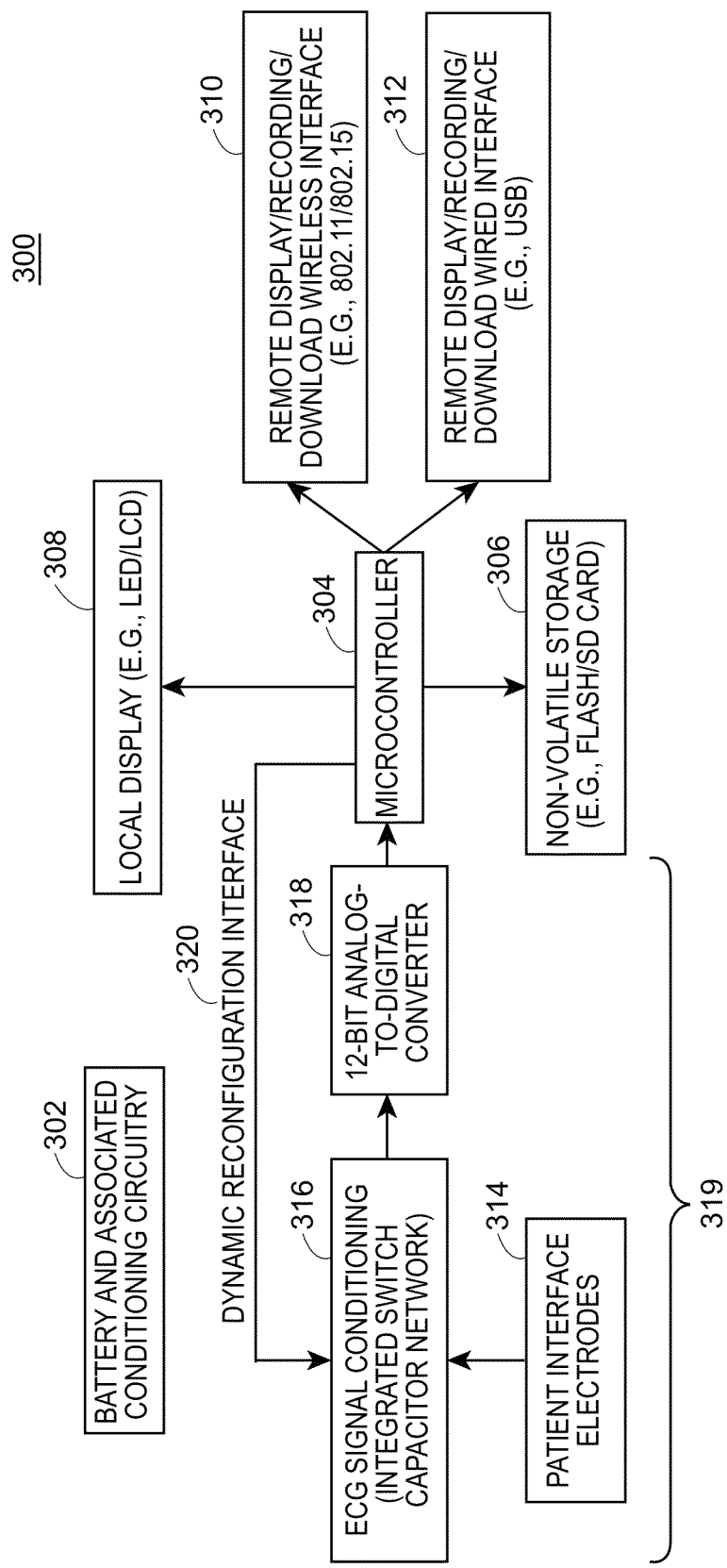
FIG. 3 is a block diagram an implementation of the ECG-based arrhythmia detection system of FIG. 1.

The atrial fibrillation classification unit 106, discussed further and illustrated in an example in FIG. 3, receive electrical signals from the unit 102 and performs an analysis on those electrical singles, including determining a spectral frequency dispersion metric (SFDM) value over a predetermined range of frequencies and then performing a heart rhythm classification based on that total normalized power values. The classification data may be stored at the unit 106 and/or transmitted to a remote computer 108 through a wired or wireless connection (WLAN) 110. Examples of wired interfaces include serial, universal serial bus (USB), or Ethernet. A WLAN compatible transceiver stage (not shown) within the device 106 may be a transceiver compliant with any one of the various IEEE 802.xx wireless standards, such as 802.15 (Bluetooth) or 802.11a, b, g, and/or n wireless LAN standards. Additionally, longer range wireless communications, such as cellular modems, WiMAX (802.16) or Mobile Broadband Wireless Access (802.20) may be used for longer ranges or direct communication with the hospital or any monitoring station/service.

The remote computer 108 may be any of a hospital, nurse's station, doctor's terminal, prescription system, or hospital administration system. And while a single such remote computer 108 is shown, a plurality of remote computes may be connected to the device. The remote computer 108 is coupled to medical records database 112 for storing historical atrial classification data for the patient and/or other atrial classification data, such as baseline data used for baselining. A display 114 is coupled to the remote computer 108, as well as output device 116 such as a peripheral printer, such as a bar code printer, line printer, image printer, etc. Other output devices may include an external database or other computer.

Figure 2A:
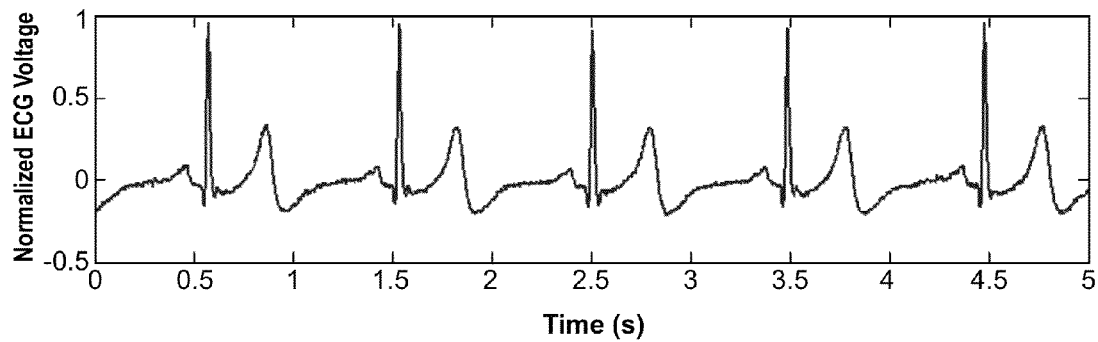
Figure 2B:
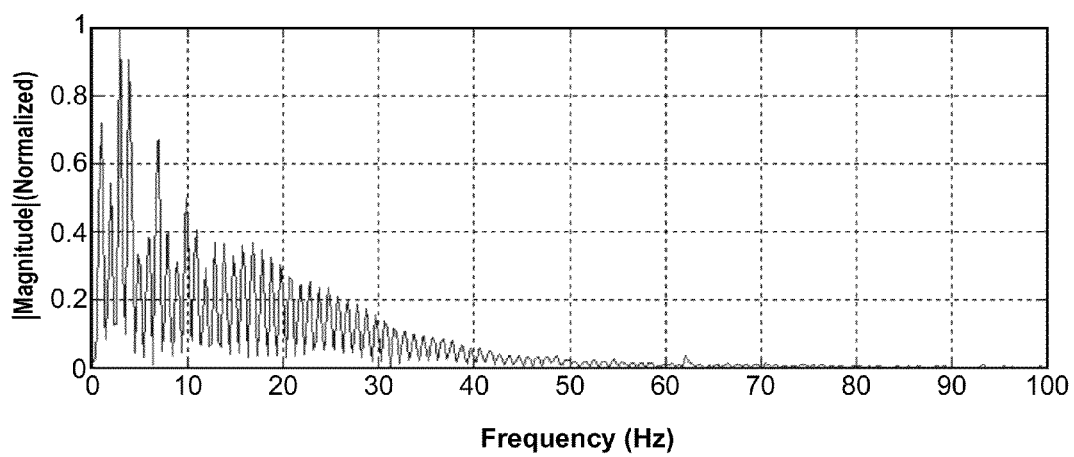
FIG. 2B is a plot of the frequency domain representation of these electrocardiogram signals.
Figure 2C:
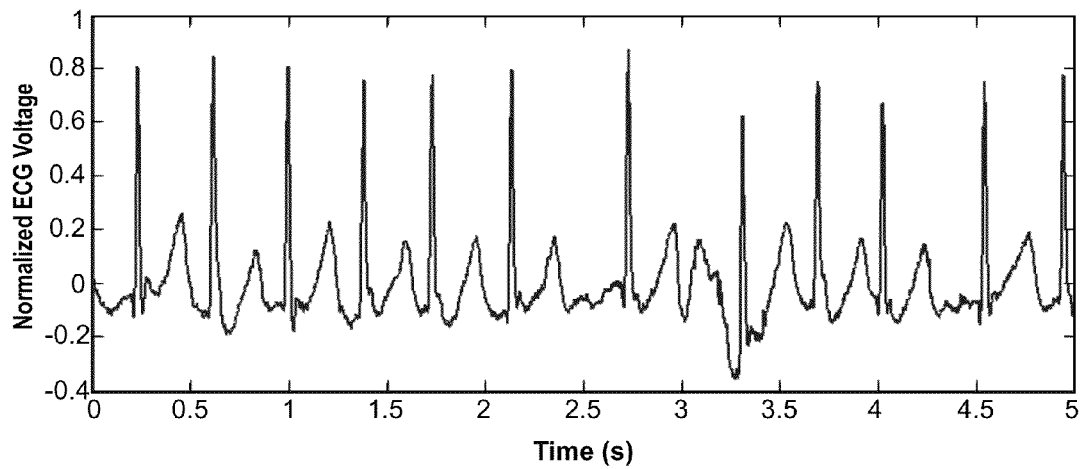
Figure 2D:
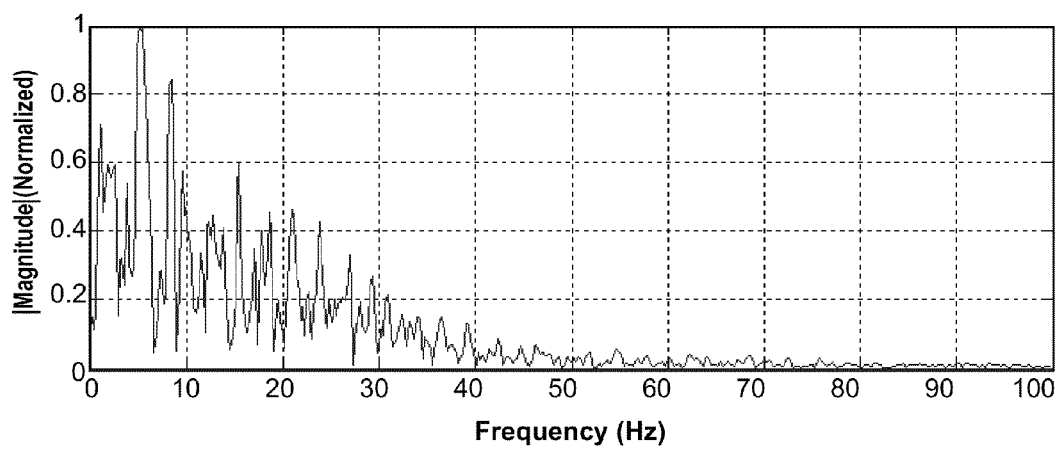
FIG. 2D is a plot of the frequency domain representation of these electrocardiogram signals.
Figure 2E:
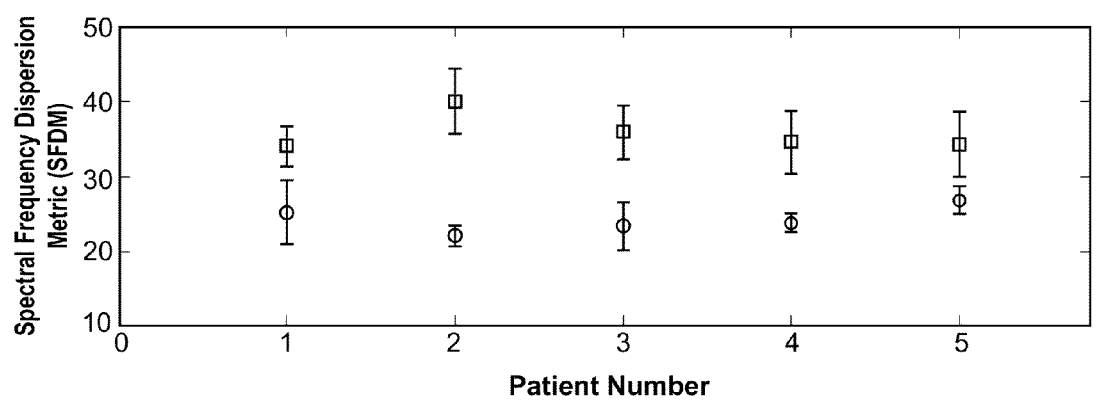
FIG. 2E is a plot of SFDM resulting from each of the frequency domain representations in FIGS. 2B and 2D, for normal patient and a patient experiencing atrial fibrillation.

FIG. 2A illustrates electrocardiogram signals, taken over a sampling period, for a patient under normal sinus rhythm. The signals are in the time domain, while FIG. 2B is a plot of the frequency domain representation of these electrocardiogram signals. FIG. 2C illustrates electrocardiogram signals, taken over a sampling period, for a patient experiencing atrial fibrillation. The signals in FIG. 2C are in the time domain, while FIG. 2D is a plot of the frequency domain representation of these electrocardiogram signals. As shown in FIG. 2E, the determined spectral frequency dispersion metric (SFDM) from each of these two different frequency domain signals varies dramatically for each of 5 different patients examined under trial, with each of the upper SFDM values corresponding to the patient when the patient is experiencing atrial fibrillation and each lower SFDM value corresponding to when the patient is not experiencing atrial fibrillation. From the illustration it is apparent that atrial fibrillation correlates to a higher SFDM compared to sinus rhythm. Also it is apparent that the difference between atrial fibrillation SFDM values and sinus rhythm SFDM values can vary greatly from patient to patient. It can also be seen that in many cases the SFDM variability is greater for atrial fibrillation than sinus rhythm states.

FIG. 3 is a block diagram of an example atrial fibrillation classification system 300 in accordance with an example and that may be used at a point of care. A battery 302, including conditioning circuitry, powers the device 300, which includes a microcontroller 304, a non-volatile storage memory 306, such as a flash memory, SD card, universal serial bus (USB) drive, etc. and a local display 308, such as an light emitting diode (LED) or liquid crystal display (LCD) device. A wireless interface 310 is also provided and includes a wireless transceiver for connecting to remote display, remote computer, and/or remote database for transmitting and receiving data and/or programming instructions. The wireless interface 310 may be compatible with any of the IEEE 802.11a, b, g, and/or n, 802.15, or other wireless standards. In the illustrated example, a wired interface 312 is also provided for connecting to a remote display, remote computer, and/or remote database, using a wired connection such as USB connection, Ethernet connection, or serial connection.

The microcontroller 304 is coupled to patient electrodes through an interface 314, which is a wired interface in the illustrated example. In the illustrated example, therefore, no separate electrode assembly 102 is used. Instead, electrodes are coupled directly to the atrial fibrillation classification device 300. In a configuration like that of FIG. 1, no wired interface 314 would be used, but instead the wireless interface 310 would be used to receive electrical signals from the patient electrodes via a wireless electrode assembly.

Received signals from the interface 314 are coupled to signal conditioning circuit 316, with integrated switch capacitor network. Example conditioning circuits include ECG signal conditioning circuits, although any conditioning circuit may be used to amplify the received electrical signal, pass the signal through a low pass filter for noise reduction, and perform any shaping on the signal to reduce flutter, jitter, and/or other noise. The conditioned electrocardiogram signal from the interface 316 is coupled to a 12 bit analog-to-digital converter 318 coupled to the microcontroller 304.

In this configuration, the blocks 314, 316, and 318 form an input stage 319 receiving an electrocardiogram signal from patient electrodes. This input stage 319 is coupled to the microcontroller 304 through a dynamic reconfiguration interface 320 to allow dynamic adjustment of the signal processing in the input stage. This dynamic adjustment includes signal amplification, DC offset removal, bandwidth adjustment of notch and bandpass filters to optimize the acquired signal.

The microcontroller 304 includes an analysis stage that receives the amplified electrocardiogram signal from the input stage, and performs various functions such as buffering the received data, performing a Fourier transform on the received data to convert the data into a Fourier domain signal. The microcontroller 304 then determines a SFDM for the Fourier domain signal, where the energy is determined over a predetermined set of frequencies and is divided by the maximum energy level. The set of frequencies may be contiguous, but need not be. Specifically selected frequencies may be used in some examples. The device used sufficient samples to perform an n point FFT, after which the additional data could be used to calculate other statistical metrics, such as means and standard deviations. From the SFDM, the microcontroller 304 performs a heart rhythm classification, identifying whether the SFDM indicates that the patient is experiencing sinus rhythm, atrial fibrillation, atrial flutter or ventricular fibrillation, which indication may be stored on the storage 306, displayed at the display 308, and transmitted continuously, periodically, or in response to poling, to a remote system through either the interface 310 or 312.

The Fourier domain signal is a frequency domain signal. In other examples, the microcontroller operates in the time domain or phase domain, from which STDM and SPDM values are determined.

Figure 4:
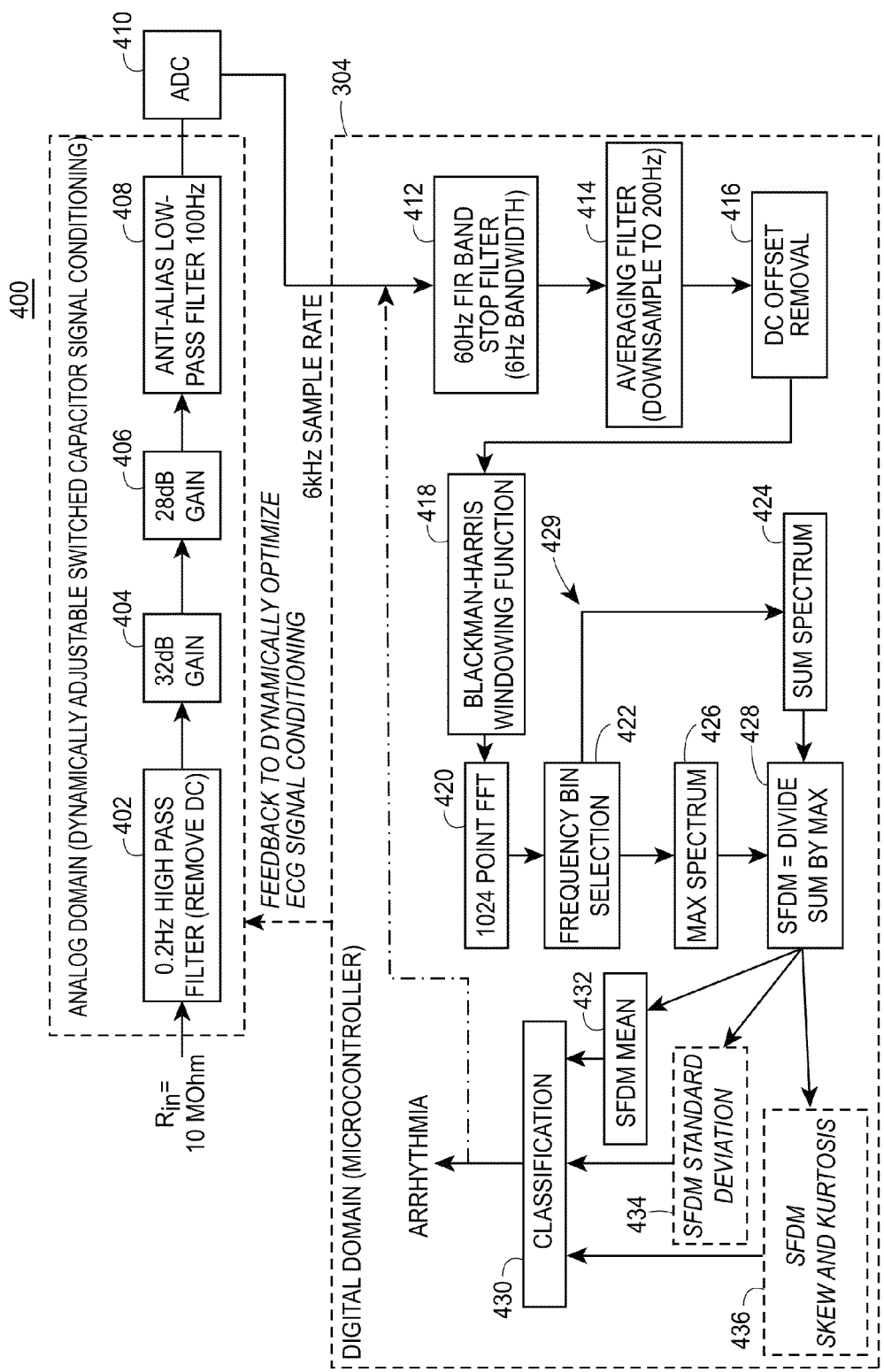
FIG. 4 is a functional block diagram of the implementation of a SDM ECG-based arrhythmia detection system of FIG. 3.

FIG. 4 illustrates a more detailed functional block diagram 400 illustrating various operations as performed by the microcontroller 304, in an example. The conditioning circuit 316 coupled to the interface 314 has an input impedance input of $R_{in}=10$ MΩ, and may be impedance matched to the interface 314. Initially, an input stage includes a high pass filter stage 402 (operating at 0.2 Hz) is used to remove a DC component from the received patient electrode signal. A first gain stage 404 (32 dB) is applied, then a second gain stage 406 (28 dB) is applied (each at or below 100× gain, in some examples) before the amplified signal is applied to an anti-alias low-pass filter stage 408. The filtered signal is passed to an ADC stage 410 that is coupled to the microcontroller 304, as shown.

The received signal is passed to a 60 Hz finite impulse response (FIR) filter 412 having a 6 Hz bandwidth that is part of an analysis stage of the controller 304. A buffering stage includes an averaging filter 414 that down samples the input signal to 200 Hz. The ADC stage 410 may sample at about 10 kHz, which is then averaged over 50 samples to reduce noise, resulting in a 200 Hz down-sampled signal. A functional block 416 removes a DC offset value from the averaged signal before the signal is passed through a windowing function 418, which applies a symmetrical function, increasing from zero to a peak and decaying back to zero to optimize the spectral estimate of the signal. In the illustrated example, a Blackman-Harris window is used, but any number of window functions may be used.

A domain transform is performed on the averaged signal, in the illustrated example by a fast Fourier transform (FFT) function 420, in this case a 1024 point FFT, as part of a transformation stage. The frequency set used for analysis is selected through a logical conjunction of the frequency domain signal and frequency bin selector mask function 422.

For example, the selector function 422 may identify a frequency range of between 0-100 Hz, and more particularly between, 0-40 Hz, and even more particularly between 3-20 Hz. The bin selector 422 is coupled to a spectrum summation function 424 that determines energy values across the frequency domain signal and sums the energy values to produce a total energy value. The frequency bin selector may focus on a weighted group of frequencies in the frequency domain, weighted group of phase-delays in the phase domain, or weighted group of times in the time domain. The frequency bin selector 422, or any of the blocks of the evaluation stage 429, may employ a search algorithm to automatically determine from the electrocardiogram signal optimal sets of frequencies to use in distinguishing between sinus rhythm, atrial fibrillation, atrial flutter and/or ventricular fibrillation. The frequency bin selector function 422 is also coupled to a max spectrum determination function 426 that determines the maximum energy across the frequency domain signal. The SFDM (or STDM or SPDM) is determined at a block 428, in the illustrated example, by dividing the summed energy from the block 424 by the maximum energy from the block 426. The blocks 422, 424, 426, and 428, therefore may form part of an evaluation stage 429, along with blocks 432, 434, and 436 discussed below, in the illustrated example. It will be appreciated that these stage indicators are provided by way of example, and that any number of the blocks may be combined in different combinations into different stages and that the descriptions herein are for convenience and explanation purposes only.

In some examples, the SFDM from the block 428 is coupled directly to a classification stage 430, while in other examples, the SFDM from the block 428 is coupled to an averaging stage 432 that determines the mean SFDM over a number of measurement cycles. The classification stage 430 may include a predetermined set of ranges for SFDM values corresponding to normal sinus rhythm, atrial flutter, atrial fibrillation, and ventricular fibrillation. For example, ventricular fibrillation may be characterized by a very sharp decrease in power at around 1-2 Hz relative to sinus rhythm. Atrial fibrillation and atrial flutter may be characterized by different alterations in the mean, standard deviation, skewness and/or kurtosis of the energy profile (power spectrum) of each cycle relative to sinus rhythm. The classification stage thus compares the received TNP value to these ranges and creates a heart rhythm classification, which signal may be displayed on the display 308, stored on the memory 306, and/or transmitted to a remote station through interfaces 310 and/or 312. The classification block 430 may deploy any suitable algorithm, of which a genetic algorithm is an example. This classification occurs automatically as described, and may be part of a learning system in which classification assessment is optimizable, either manually through operator adjustment, in a semi-automated manner, or a fully-automated manner.

In some examples, additional analysis of the SFDM data is used to strengthen the classification determination, in particular where more than three different classifications are used. For example, additional statistical metrics may be used to extract time-domain statistics of the SFDM metric. The data can be used to provide a more robust prediction by improving accuracy though the evaluation of other features of the signal. For example, the SFDM data from block 428 may be provided to a SFDM standard deviation function 434 which provides the SFDM data to the classification stage 430. In another example, the SFDM block 428 is coupled to another statistical metric block 436 that performs a skew, kurtosis, or other statistical operation on the data designed to further reduce extraneous signal components before the SFDM data are sent to the classification stage. While the illustrated example uses a FFT, other implementations may be achieved. For example, one could use an field programmable gate array (FPGA) with a parallel arrangement of digital band pass filters to allow real-time parallel computation of the classification result. Another example would be to design an integrated circuit with a parallel array of analog band pass filters, feeding into an analog summing stage and comparator, to provide a completely analog implementation thereof.

These are examples of how multiple feature extractions may be performed over time to produce statistics metrics for the SFDM, STDM and/or SPDM prior to classification at a classification stage. In some examples, those multiple feature extractions may be performed on frequency, time, or phase domain representations (i.e., on converted spectral dispersion of the frequency, time, or phase, respectively) to produce statistics metrics prior to determination of the SFDM, STDM, and/or SPDM, and thus prior to classification at the classification stage.

In some examples, the classification stage 430 receives a single feature or vector such as the SFDM. In the case of a single feature (e.g., SFDM) the classification may be achieved by a threshold function. However, in other examples, more features may be supplied to the classification stage 430. In such examples, the received vector may be applied to a system of equations implemented using a suitable means (i.e. regression, neural network, linguistic expression, etc.) to produce either/or both a binary classification output and continuous measure of the severity or probability the patient is in AF. An example of this may be if both the SFDM and the kurtosis of the SFDM over time are used as inputs to the classification stage 430. If these features were not combined (i.e., using a regression function) into a single metric again, a 2D classification surface would result. If SFDM values for distinct cardiac states were displayed as a scatter plot, ideally, discrete clusters would be seen. A classification function (i.e. linear, spline, circle, etc.) could be used to describe these regions allowing the device to report the current cardiac state a patient was in, given their ECG. Therefore, the classification stage 430 may comprise an additional 2 sub-stages, 1) additional transformation, for example through a regression function, and 2) multi-dimensional segmentation of the clusters describing various cardiac states.

Figure 5:
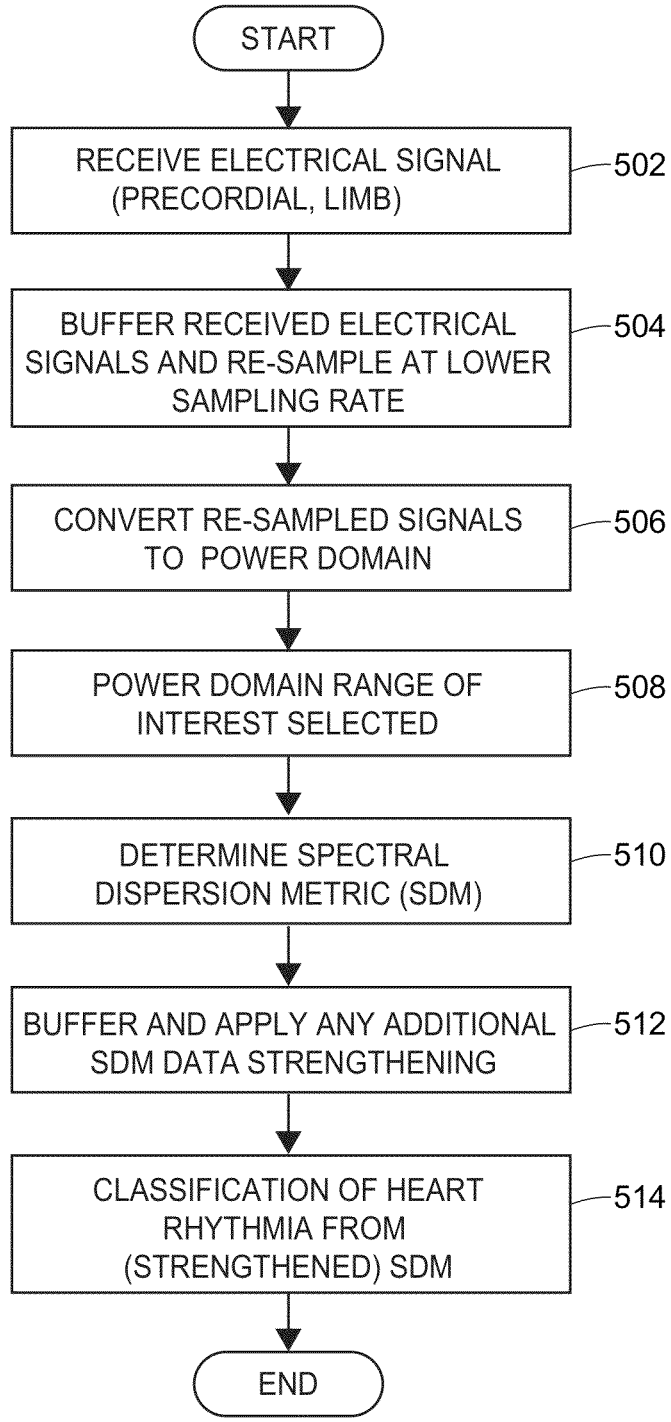
FIG. 5 is a flow diagram of an example arrhythmia detection process using the SDM method.

FIG. 5 illustrates a process 500 as may be implemented by the classification device 300. Initially, at a block 502, input signals, such as electrocardiogram signals, are received from electrodes, as may be received by the electrodes interface 314, and any signal conditioning is performed, where such signal conditioning may be performed in a separate dedicated circuit device, within a single or multi-processor device or utilizing some form of logic device, either in analog or digital form. Because the electrocardiogram signals are collected and analyzed in real time, detection and analysis may be performed in real time. For implementations into lower-power devices, the data can be captured and the analysis and classification performed at sub-real time speed. To facilitate signal analysis at cycle times needed for energy summation and classification, the collected real-time data is buffered at a block 504 and then re-sampled at a lower sampling rate. The re-sampled signals are transformed to a power conversation domain by a block 506. For example, at the block 506, the classification device 300 may perform a Fourier transform on the re-sampled electrical signals, collected in a time domain, into frequency domain signals. In FIG. 3, a fast Fourier transform (FFT) is performed by the element 420, for example. Transformation is performed to isolate the electrocardiogram signals into signal components for energy measurement. As such, the block 506 may perform a transformation into any suitable domain, which may include the phase domain using the FFT.

Other example transformations include the continuous wavelet transform, which is able to construct a time-frequency representation of a signal with improvements in time and frequency localization compared to standard FFTs. Another technique is time-frequency reassignment, which can be used to overcome the tradeoff between the time and frequency resolution associated with the short-time FFT. This technique refocuses the time-frequency data by mapping the data to time-frequency coordinates that are nearer to the true region of support of the analyzed signal.

In the illustrated example, the spectral conversion domain signals are passed to a block 508, which determines the bandwidth of the domain signals and whether a desired sub-band range exists. The block 508, for example, may be executed by the frequency bin selector 422 containing a predetermined frequency range over which power values are to be totaled.

At a block 510, the device 300, e.g., the elements 426, 424, and 428, determines the power spectrum over the domain signals and more specifically summed energy across the predetermined domain range. This range may be normalized by the highest energy level, for example as discussed above in regards to element 428, or classification may be performed over un-normalized data. It has been determined by the present inventors that summed energy over a particular range of frequency components correlates with different states of heart rhythm, in particular with different cardiac arrhythmia conditions. Instead of conventional techniques that determine a dominant frequency among the domain signals, the present technique may avoid determining dominant frequencies and instead determine total energy over a range of frequencies. That summed energy may be absolute summed energy. While in other examples, the domain signals are passed through a threshold process, e.g., at block 510, that identifies only those frequencies having a summed energy above a threshold, which are then summed to determine total energy.

Because summed energy is used, problems with low signal-to-noise in conventional systems are avoided, allowing for more accurate determinations of atrial fibrillation. Issues with the drive circuitry pulsing altering sensed electrocardiogram signals is reduced or eliminated, as is operator subjectivity, which can affect measurements in conventional systems. Also, because energy (power) is determined over a minimal set of data (e.g. 0-20 Hz) the ultimate classification is more robust because it focuses on a known, previously analyzed classification spectrum region. The summed energy technique also does not require altering the electrocardiogram signals, by the subtraction of the ventricular activity (i.e., the QRS and T complexes of the ECG); although, such subtraction may still be performed. Further still, the sampling of summed energy is typically performed at a lower sampling interval, e.g., every 3-5 seconds, reducing the computational demand, compared to more real-time systems. This also allows for the implementation entirely in hardware and/or software. Furthermore, the present techniques have low latency times between summed energy measurements. Latency times below 1 s have been shown in some examples. Furthermore, electrical lead placement is not critical for the summed energy determination, as electrocardiogram signals may be recorded by any lead configuration whether leads are placed precordially or on the limbs.

Optionally, a block 512 may buffer summed energy data over a period of time and perform additional analysis on that data, including determining standard deviation of the summed energy values (with or without normalization) and then performing skew or kurtosis shaping to isolate the buffered data further.

At a block 514, the SFDM data is analyzed to determine which classification of heart rhythm the data corresponds, thereby indicating whether the patient is experiencing sinus rhythm, atrial flutter, atrial fibrillation, and ventricular fibrillation.

The SFDM may be determined from electrocardiogram signals collected from a single location, as discussed above, or from multiple locations. For example, the multiple electrode pairs may be placed simultaneously in the precordial region and on one or more limbs, from which a classification device is able to determine SFDM over a range of regions. In such examples, scaling of summed energy values in different regions may be used to account for inherently different energy levels. Determinations based on STDM and SPDM would follow accordingly.

In other examples, classification devices are able to isolate summed energy measurements at different locations that are each, individually calibrated to heart rhythm classification. In such examples, certain summed energy values measured at the precordial regions may indicate a first heart rhythm condition, while those same normative summed energy values at a limb may not indicate the first heart rhythm condition, but another.

FIG. 4 illustrates an AF classification system capable of detecting an arrhythmia condition in a patient and assessing the type of corresponding arrhythmia, e.g., atrial fibrillation, ventricular fibrillation, atrial flutter, or another arrhythmia. In various examples, the AF classification devices herein provide patient-specific customization, health condition specific customization, and/or health care provide specific customization. In some examples, the devices provide for optimization in AF assessment, either through a fully manual adjustment by an operator or healthcare professional or through semi-automated or fully-automated adjustments. In these ways, the devices herein may be tailored to individualized operation, for example, as part of a learning system.

Figure 6:
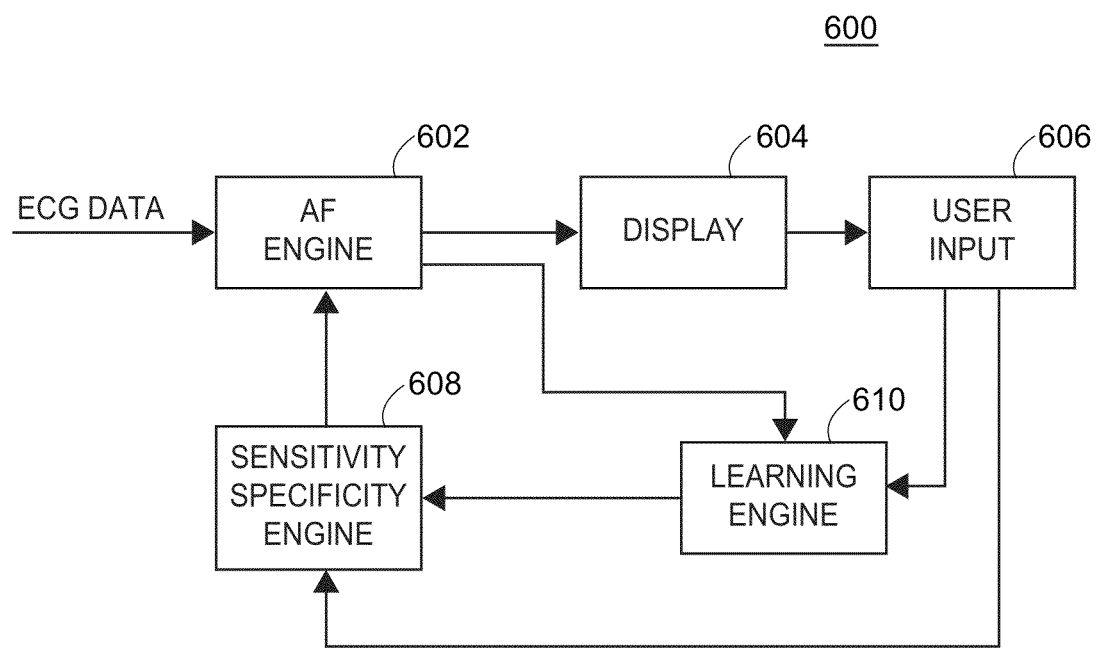
FIG. 6 is a block diagram of an example optimization and customization of an ECG-based arrhythmia detection system.

FIG. 6 illustrates an example learning atrial fibrillation system 600 composed of an AF engine 602, for example, operating in accordance with the AF system 400 in FIG. 4, that receives ECG signals data for the heart. The ECG data is provided to the AF engine 602, like ECG data would be provided to the $R_{in}$ input line of the signal conditioning circuit of FIG. 4, from which an AF determination and classification is made in a similar manner to that of the classification engine 430. In the system 600, AF classification data is provided to a display 604 having an input device (touch screen, stylus, keyboard, mouse, keypad, etc.) allowing for user interaction. In some examples, the display 604 may provide a visual indication of the classified AF condition, ECG data, SFDM, STDM or SPDM data, and/or total normalized energy values plotted in real time or over time.

The display 604 presents the data to the user, who is able to respond by manually optimizing operation of the AF engine 620, through a user input 606. For example, the display 604 may present the user with the AF data and an interface, in response to which the user, at the block 606, determines a suggested change in the specificity and/or sensitivity of the AF engine 602. If the user determines that a change in specificity and/or sensitivity is desired then a control signal is sent to a sensitivity and specificity engine 608 that sends a control signal to the AF engine 602 modifying operation thereof.

In this way, the system 600 may analyze the characteristics of diagnostic metrics utilized to discriminate the arrhythmias for each patient. Based on the distribution of measured metrics from the ECG, for example, the thresholds or other metric criteria used to classify different rhythms as normal, sinus rhythm, atrial fibrillation, ventricular fibrillation, flutter may be adjusted to optimize the diagnostic accuracy of the system for each patient individually. This may be accomplished with a user input interface, e.g., where the display 604 provides an operator/physician a scattergram of the distribution of the metrics from the engine 602.

In manual operation, the operator/physician may manually adjust thresholds or other metric criteria based on the scattergram data. In a semi-automated manner, the sensitivity and specificity engine 608 may determine, from the AF data of AF engine 602, a suggested threshold or other metric criteria that matches an initial desired sensitivity and specificity range. This suggested value or suggested operating range is then provided back to the AF engine 602 and overlayed (or otherwise displayed) to the user along with the AF data on the display 604. The user may then, at block 606, accept the suggested value(s) (thresholds or other metric criteria) or make manual adjustments thereto, to thereby alter the sensitivity/specificity of the AF engine 602. In a fully automated operation, the engine 608 may, not only, automatically determine the suggested threshold or other metric criteria for making the AF assessments, but then automatically adjust the AF engine 602 to operate in accordance with those conditions, i.e., without user input. Applying these techniques to that of FIG. 4, for example, the engine 608 may adjust any of the metrics used by blocks 422-430 to optimize or otherwise customize operation of the classification at block 430. For the semi-automated or fully-automated modes, a learning engine 610 is provided to receive the output AF data from the engine 602 and any other patient related dated, whether real-time data, historical data, or otherwise. That learning engine 610 may automatically provide control signals for adjusting the sensitivity and specificity at the engine 608, or it may do so under control of the user via input 606.

Thus, the system 600 is able to optimize sensitivity and specificity of the determination of any rhythm to account for possible false positives and false negative results according to the clinical condition and requirement set forth by a clinician's discretion. For example, when a patient has a stroke risk higher than bleeding risk, then the detection of AF and use of anti-coagulants could be determined with a higher priority on sensitivity over specificity (100% sensitivity guaranteed). If on the other hand, a patient's highest risk is of bleeding, then the priority is specificity over sensitivity (100% specificity guaranteed). Such adjustments can be made through manually, semi-automated, or fully automated adjustments.

Figure 7A:
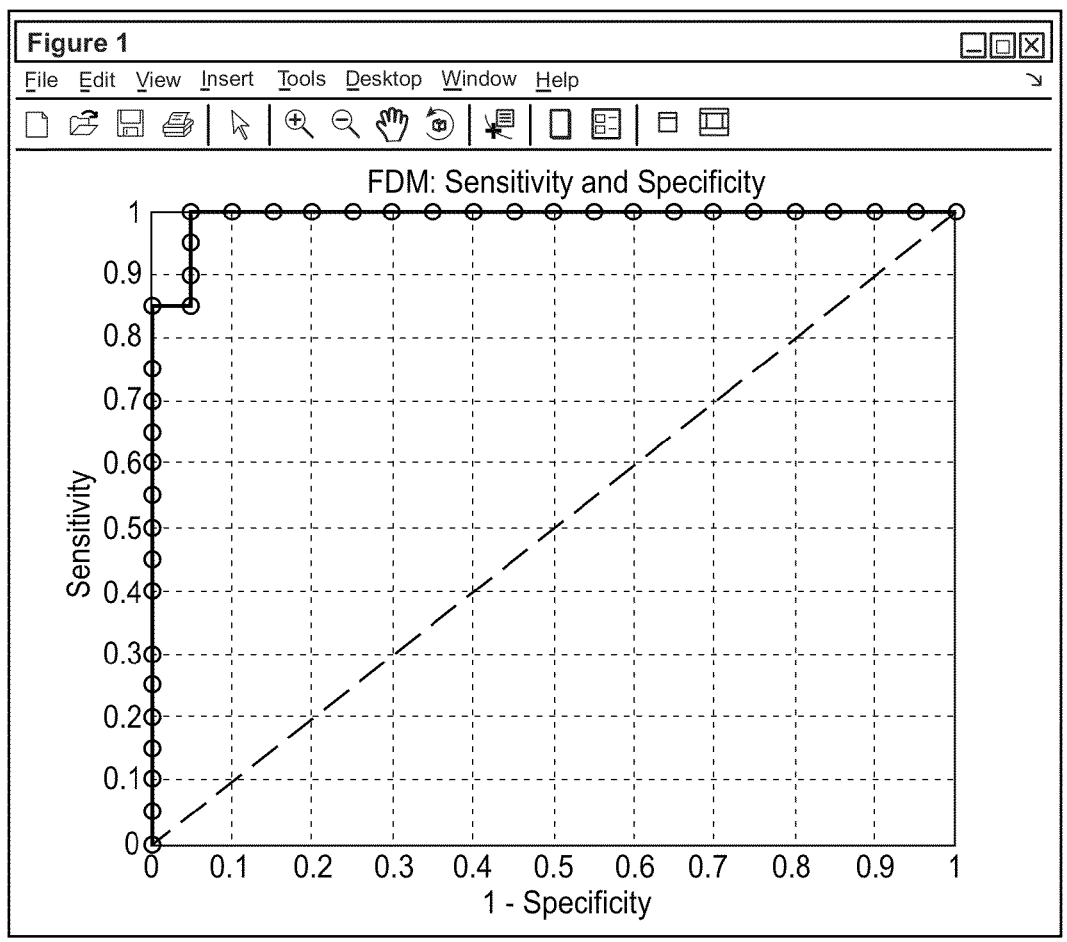
FIGS. 7A-7C are plots of scattergrams used in optimizing and customizing the arrhythmia detection system of FIG. 6 according to an example.
Figure 7B:
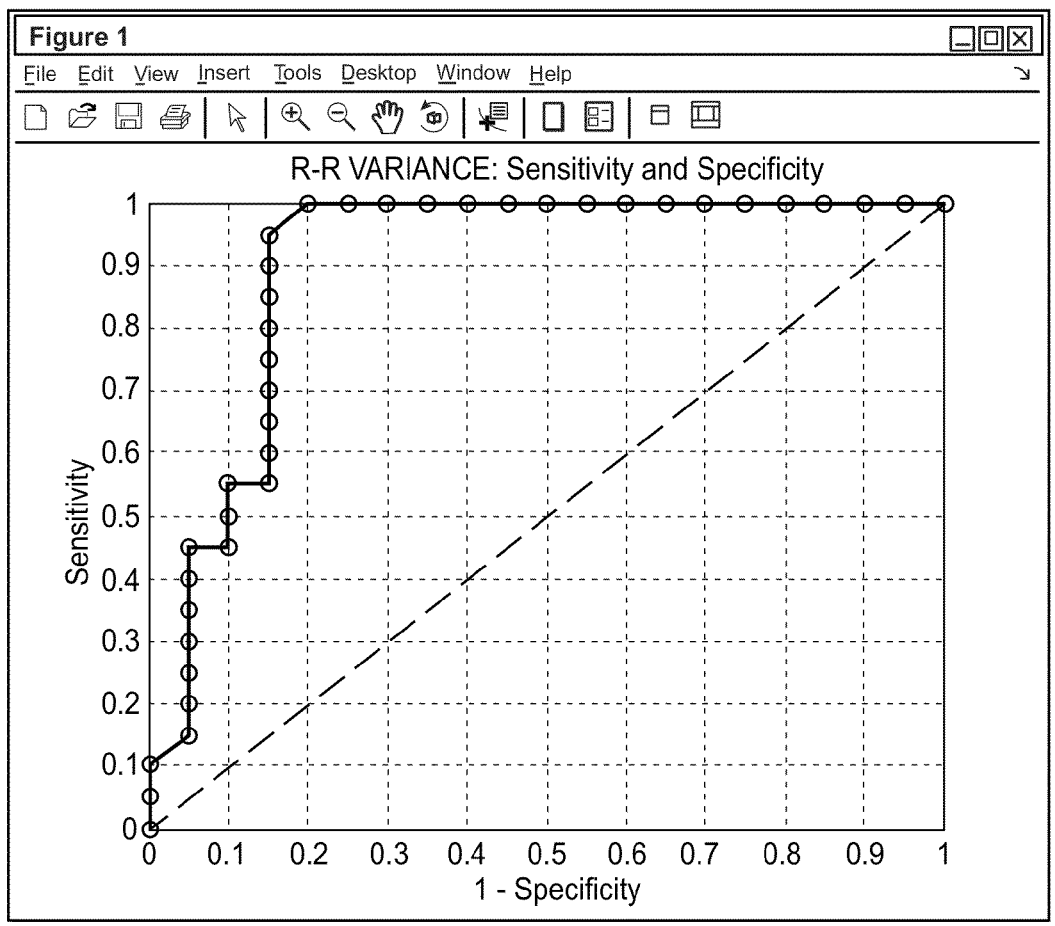
Figure 7C:
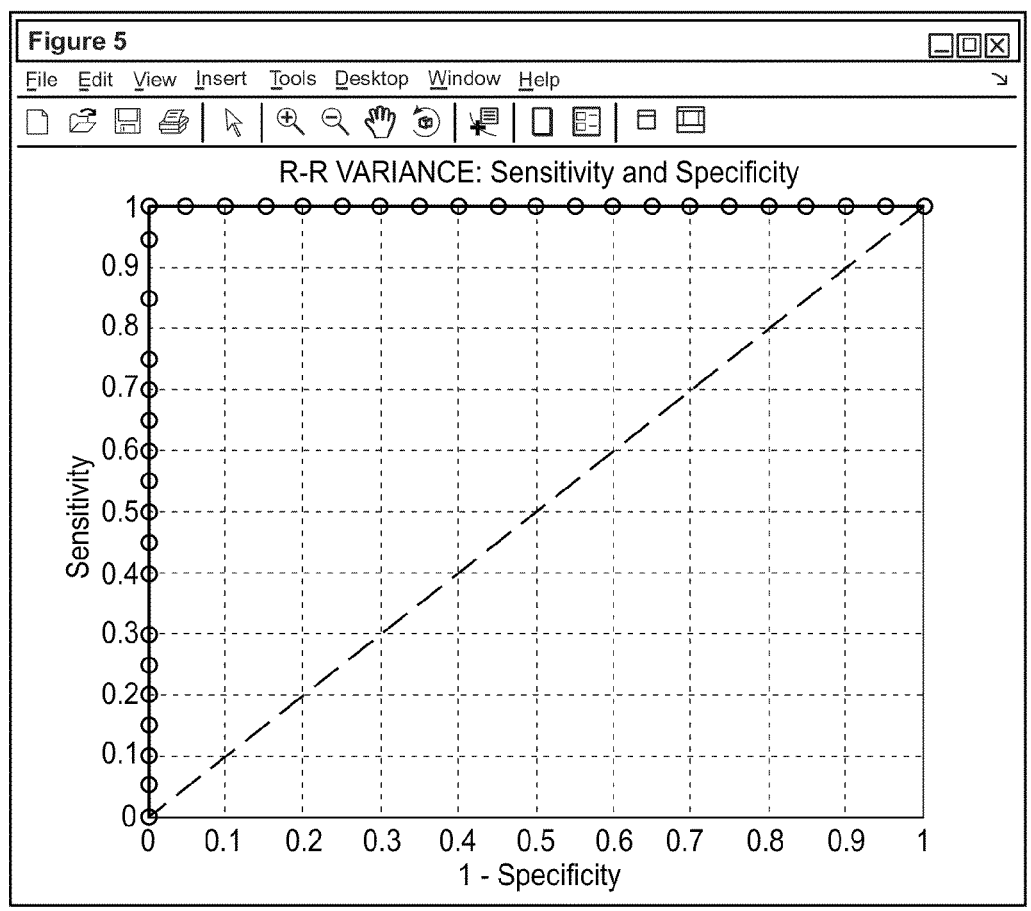

FIGS. 7A-7C illustrate sensitivity-specificity analyses (Receiver operating characteristic, ROC, curves) for a binary detection of AF based on scattergram plots (an example of a scattergram of frequency domain analysis, SFDM, is presented in FIG. 2E) in three different metrics or databases, each having a full range of metric discriminating thresholds for assessing the presence of AF with different accuracy. The ROC curve illustrates the fraction of true positives (sensitivity) versus the fraction of the false positives (1-specificity) for sample ECG events for a group of patients. In FIGS. 7A and 7B, the data from a miss-classified patient is included in the database, reducing the overall accuracy of either SFDM (FIG. 7A) or RR-interval variance (FIG. 7B) metrics and requiring adjustment of threshold to maximize sensitivity or specificity alternatively. When the total power threshold is adjusted to exclude this miss-classified person (e.g., using the system 600), the ROC curve changes to that of FIG. 7C, demonstrating the ability of SFDM metric to achieve a 100% sensitivity and specificity simultaneously; the ideal condition for AF detection and classification. The plots of FIGS. 7A-7C may be provided to the user on the display 604 along with an user input interface for adjusting thresholds or other metrics that result in changes in the scattergram. It will be understood that the plots are provided by way of example and that while adjusting a single threshold is discussed in the illustrated example, any number of metrics may be adjusted by the user as desired. Similar types of optimization of AF data sets would be performed on single patient data as well.

The ECG data and AF data collected for patients may be used for individualized patient or group data mining. Patient data, whether collected from an handheld AF classification device, electrocardiographic recording system, or otherwise, is stored in a database. A data mining engine may analyze the database, e.g., in an "ECG-informatics" manner deploying a genetic algorithm, to identify hard-to-notice, hidden, correlations of temporal, spectral and phase patterns, within the patient data. This data mining could include identifying metrics calculated in those domains, such as total energy over specified domain ranges. The patient data would be collected across episodes of cardiac electrical activity of various rhythms and properties. Those episodes could be episodes belonging to the same patient at different times, frequencies and/or phases, or those belonging to different patients as part of a population study. In some examples, the data mining engine may search for patterns across ECG data to identify 'hidden' occurrences, e.g., in the converted frequency, time, or phase domain of that ECG data, that correlate to different AF classifications. Such occurrences thus may determine indicators that are more nuanced or more complex than the threshold and other metrics discussed herein, or that are more multivariate than would be the case for initial AF classification algorithms. Such data mining thereby may be used along with the adapting algorithms described herein, e.g., the genetic algorithms that may be implemented by the AF classification block 430, to provide historical data-based optimization and customization of AF assessment. One of the advantages of using historical data in this manner is that additional patient data, including data external to the AF classification systems described herein and otherwise believed irrelevant to AF classification may also be provided and considered by the system. Examples of such data include patient demographic data (e.g., age, gender, ethnicity, etc.), physiological data (e.g., weight, heart size, blood pressure, etc.), and time course of cardiac function (e.g., ECG time-series, ECG intervals, heart rate, incidences of extrasystoles, AF, heart rate variability (HRV) parameters, heart rate turbulence, etc.)".

Figure 8:
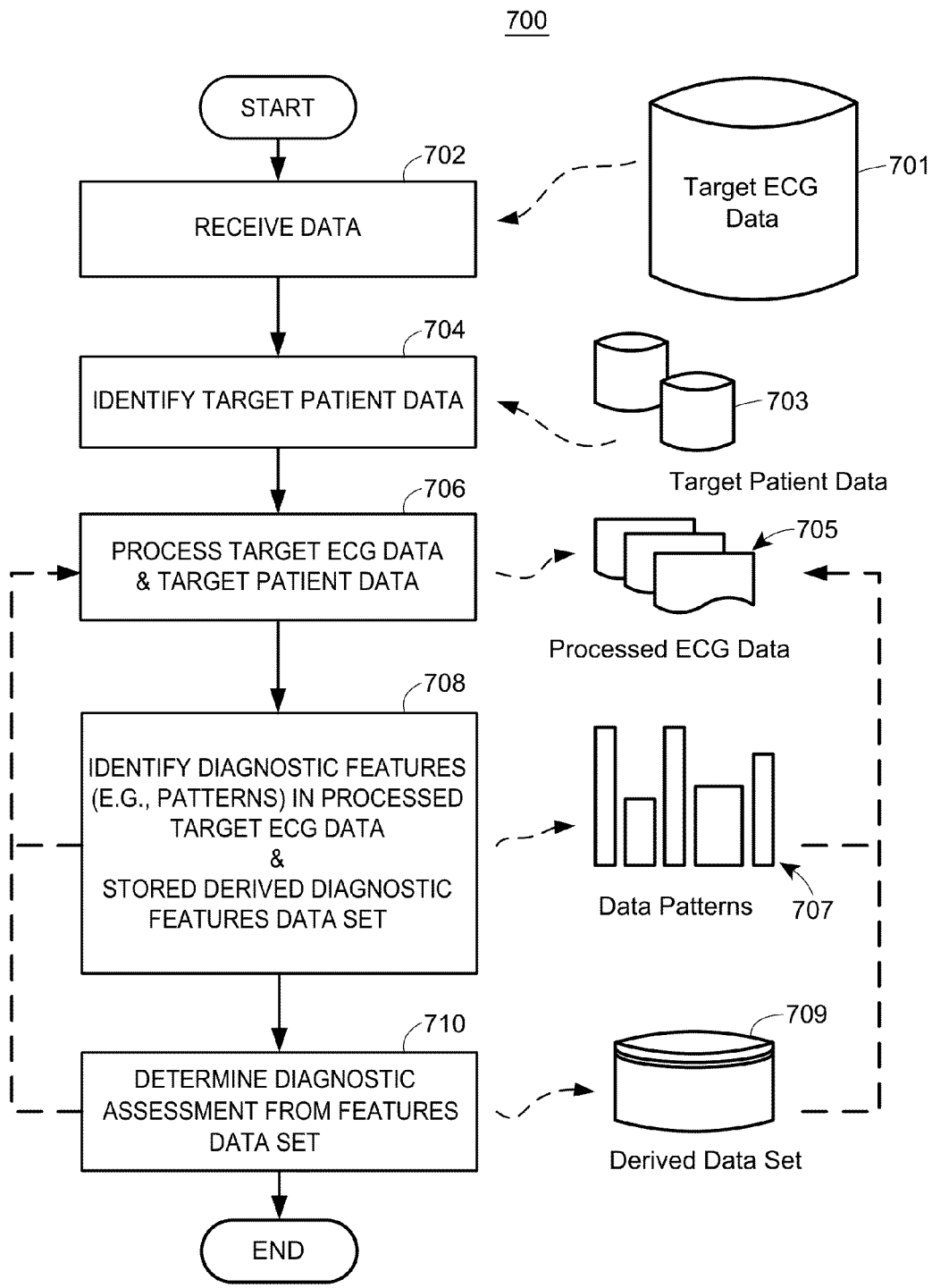
FIG. 8 is a flow diagram of an example process to perform data mining and diagnoses on patient data, such as ECG-based data, according to an example.

FIG. 8 illustrates an example process 700 to perform data mining on patient collected data, in accordance with an example and as may be implemented on a computer system. The process 700 may be executed on an analysis machine, such as any classification machine described herein, e.g., that of FIGS. 3 and 4. Although, the analysis machine may be used in the diagnosis of any number of conditions, arrhythmias and non-arrhythmia conditions.

A block 702 receives initial patient data, such as raw data like a target ECG data stored in a database 701, and/or other patient data, as described herein. A block 704 identifies target patient data 703 within the broad data from block 702. For example, the block 704 may include instructions to target a specific patient or patient group, based on any number of desired patient traits, including demographic traits, physiological data, historical data, or otherwise. The block 704 would in some examples include predetermined instructions for identifying a target group, while in other examples the block 704 may require input from a physician or other healthcare professional to provide characteristics of target patient data to be examined. A block 706 may perform processing on the targeted ECG data corresponding to the target patient data, producing processed ECG data At a block 708, desired diagnostic features in the processed target ECG data are identified and stored in a diagnostic features data set 707. The block 708 may execute adapting algorithms to mine the ECG data (and other patient data) for features corresponding to a potential diagnosis. Features for diagnosing arrhythmias are described hereinabove, but the block 708 is not limited to diagnosing arrhythmias. Instead, the block 708 may identify any number of features corresponding to any number of diagnosable conditions. Preferably, the diagnostic features may be frequency, time or phase domain features, summed energy values determined over range of frequencies, time intervals or phases for these domain features, SFDM, STDM, and/or SPDM, for example. The identified diagnostic features set 707 may be multi-variant, meaning that the features may include a plurality of features. For example, the block 708 may identify a feature in the target ECG data for certain patients that corresponds to a physiological feature of those same patients, like weight, heart size, blood pressure, ECG time-series, ECG intervals, heart rate, incidences of extrasystoles, AF, heart rate variability (HRV) parameters, heart rate turbulence, etc. The block 708 may execute an adapting algorithm that recursively mines through the data provided thereto for correlations in the patient, patterns (as shown as 707) in the patient data, that are then stored as the diagnostic features data set.

At a block 710, a diagnostic assessment is made from the diagnostic features data set from block 708. When mined for assessing arrhythmia, the block 710 may identify an arrhythmia classification from the data mining, thereby offering the potential to classify arrhythmias based on heretofore un-known patterns across patient data (ECG data, physiological data, demographic data, etc.). The block 710, also capable of executing an adapting algorithm, may thus provide hard-to-notice, hidden, correlations of temporal, spectral and phase patterns, including metrics calculated in those domains, between episodes of cardiac electrical activity of various rhythms and properties. Such diagnoses can be stored as a derived data set 709, constructed from targeted ECG data and other patient data. As a data mining system, whether adaptive or not, the blocks 706-710 may be executed by the computer system in a recursive manner, as indicated by the dashed lines, allowing for iterative-based identification and diagnoses.

The present techniques may be used in standalone classification devices, as described, as well as in integrated atrial fibrillation mapping systems. Conventional mapping systems determine dominant frequencies and locations of dominant frequencies for mapping the heart tissue to identify arrhythmia source sites. The dominant frequency data, in such systems, is used as domain data from which, separately frequency selection is performed, to identify frequency ranges of interest, and then summed energy values are determined. These configurations include catheter based mapping systems as well as 3 dimensional electrode arrays which may be used endocardially or epicardially. The present techniques may also be used with atrial fibrillation treatment assemblies, such as ablation devices, serving as a real-time assessment of treatment effectiveness by measuring electrocardiogram signals and determining summed energy and classifications during or after treatment. The techniques may be used before treatment as well, of course.

The techniques may be implemented in devices external to the patient, using externally mounted ECG leads. While in other examples, the devices may be implantable, for example, adjacent the heart. The devices may be included in an implantable cardiac defibrillator device, for example, for detection of AF conditions (e.g., ventricular fibrillation) and used in the controlled delivery of fibrillation therapy. The devices may be contained within an automated internal or external defibrillator for detection of AF conditions (e.g., ventricular fibrillation) and to control delivery of fibrillation therapy.

The various blocks, operations, and techniques described above may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any computer readable memory such as on a magnetic disk, an optical disk, or other storage medium, in a RAM or ROM or flash memory of a computer, processor, hard disk drive, optical disk drive, tape drive, etc. Likewise, the software may be delivered to a user or a system via any known or desired delivery method including, for example, on a computer readable disk or other transportable computer storage mechanism or via communication media. Communication media typically embodies computer readable instructions, data structures, program modules or other data in a modulated data signal such as a carrier wave or other transport mechanism. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Thus, the software may be delivered to a user or a system via a communication channel such as a telephone line, a DSL line, a cable television line, a wireless communication channel, the Internet, etc. (which are viewed as being the same as or interchangeable with providing such software via a transportable storage medium).

Moreover, while the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

What is claimed is:

1. An apparatus for detecting arrhythmias within a body, the apparatus comprising:

an input stage to receive an electrocardiogram signal from a body connected thereto through a detection electrode input, wherein the input stage is a real-time dynamically adjustable signal transformation stage configured to condition the electrocardiogram signal;

an analysis stage coupled to the input stage to receive the conditioned electrocardiogram signal from the input stage, wherein the analysis stage comprises, a transformation stage wherein a frequency, time, or phase domain representation of the conditioned electrocardiogram signal is formed from the conditioned electrocardiogram signal being in a time-domain signal, and an evaluation stage, wherein frequency, time or phase domain features related to the arrhythmias are extracted from the frequency, time, or phase domain representation, wherein the evaluation stage is configured to determine a summed energy over a predetermined range of frequencies, time intervals or phases for the frequency, time, or phase domain representation and configured to normalize the summed energy to the energy at the frequency within the predetermined range of frequencies having the maximum energy to form a spectral frequency dispersion metric (SFDM), spectral time domain dispersion metric (STDM), and/or spectral phase domain dispersion metric (SPDM) over the predetermined range of frequencies, time intervals, or phases; and a classification stage coupled to the evaluation stage to receive the SFDM, STDM, and/or SPDM and to determine whether the body is experiencing the arrhythmias.

2. The apparatus of claim 1, wherein the arrhythmias comprise atrial fibrillation, ventricular fibrillation, atrial flutter, or other arrhythmia.

3. The apparatus of claim 1, wherein the input stage is configured to condition the electrocardiogram signal by filtering, amplifying, and/or digitizing the electrocardiogram signal.

4. The apparatus of claim 1, wherein the transformation stage further includes:
 a buffering sub-stage for buffering the conditioned electrocardiogram signal;
 a Fourier transform sub-stage coupled to the buffering stage for converting the buffered electrocardiogram signal into a Fourier domain signal; and
 a filtering stage to select certain frequencies or bands of frequencies of the buffered electrocardiogram signal.

5. The apparatus of claim 4, wherein the buffering sub-stage comprises an averaging sub-stage and an offset sub-stage, wherein the averaging sub-stage accumulates electrocardiogram signals over a buffer time window and averages the accumulated electrocardiogram signals.

6. The apparatus of claim 1, wherein the evaluation stage is configured to perform multiple feature extractions over time and produce statistics metrics for the SFDM, STDM and/or SPDM prior to classification at the classification stage.

7. The apparatus of claim 1, wherein the evaluation stage is configured to determine at least one of a mean, standard deviation, a skewness and a kurtosis of the SFDM, STDM and/or SPDM.

8. The apparatus of claim 7, wherein the classification stage is coupled to the evaluation stage to determine whether the body is experiencing sinus rhythm, atrial fibrillation, atrial flutter or ventricular fibrillation based on the SFDM and at least one of the standard deviation of the SFDM distribution, the skewness of the SFDM distribution, or the kurtosis of the SFDM distribution.

9. The apparatus of claim 1, wherein the frequency, time, and/or phase domain representations is a frequency domain representation, composed of a weighted group of frequencies.

10. The apparatus of claim 1, wherein the frequency, time, and/or phase domain representation is a phase domain representation.

11. The apparatus of claim 1, wherein the frequency, time, and/or phase domain representation of the conditioned electrocardiogram signal is composed of a weighted group of phase-delays.

12. The apparatus of claim 1, wherein the input stage and the analysis stage are spatially separated from one another and connected through a wireless communication medium.

13. The apparatus of claim 1, wherein the analysis stage is coupled to the input stage to statically or dynamically adjust, in real-time, the conditioning of the electrocardiogram signal in the input stage.

14. The apparatus of claim 1, wherein the predetermined range of frequencies is between 0-100 Hz.

15. The apparatus of claim 1, wherein the predetermined range of frequencies is between 0-40 Hz.

16. The apparatus of claim 1, wherein the predetermined range of frequencies is between 3-20 Hz.

17. The apparatus of claim 1, wherein the evaluation stage is to utilize different portions of the frequency, time, and/or phase domain representation sets to distinguish between sinus rhythm, atrial fibrillation, atrial flutter and/or ventricular fibrillation.

18. The apparatus of claim 1, wherein the evaluation stage uses a search algorithm to automatically determine from the electrocardiogram signal optimal sets of frequencies to use in distinguishing between sinus rhythm, atrial fibrillation, atrial flutter and/or ventricular fibrillation.

19. The apparatus of claim 18, wherein the search algorithm is a genetic algorithm.

20. The apparatus of claim 1, wherein the evaluation stage is to determine a maximum spectrum spread difference between sinus rhythm, atrial fibrillation, atrial flutter, and/or ventricular fibrillation from identified discrete frequency components of the frequency, time, and/or phase domain representation within the range of frequencies.

21. The apparatus of claim 1, wherein the classification stage accesses a stored plurality of SFDM ranges each corresponding to a different arrhythmia, the classification stage being configured to compare the SFDM received from the evaluation stage to the stored plurality of SFDM ranges to determine the type of arrhythmia experienced by the body.

22. The apparatus of claim 1, wherein the classification stage receives a single feature or vector of transformed features from the transformed time-domain or frequency-domain signal.

23. The apparatus of claim 1, wherein the input stage is an analog conditioning circuit.

24. The apparatus of claim 23, wherein the analysis stage is a digital circuit coupled to the analog conditioning circuit to sample the conditioned electrocardiogram signal at a sampling rate.

25. The apparatus of claim 1, wherein apparatus is an implantable device.

26. The apparatus of claim 25, wherein the implantable device is contained within an implantable cardiac defibrillator device for detection of ventricular fibrillation and to control delivery of fibrillation therapy.

27. The apparatus of claim 1, wherein the apparatus is contained within an automated internal or external defibrillator for detection of ventricular fibrillation and to control delivery of fibrillation therapy.

28. The apparatus of claim 1, further comprising:
 a memory for storing electrocardiogram signal data, SFDM, STDM, and/or SPDM data, and a classification determination data; and
 a wireless transceiver to automatically transmit the electrocardiogram signal data, the SFDM, STDM, and/or SPDM data, and the classification determination data to a remote server through a wireless communication medium.

29. The apparatus of claim 1, further comprising:
 a learning engine configured to receive an atrial fibrillation (AF) classification determination from the classification stage; and a sensitivity and specificity engine coupled to the learning engine, wherein in response to a control signal from the learning engine, the sensitivity and specificity engine adjusts the sensitivity and/or specificity of the classification stage.

30. The apparatus of claim 1, further comprising:
a user input interface to receive an atrial fibrillation (AF) classification determination from the classification stage; and
a sensitivity and specificity engine coupled to the user input interface, wherein in response to a control signal from the user input interface, the sensitivity and specificity engine adjusts the sensitivity and/or specificity of the classification stage.

31. An apparatus for detecting arrhythmias within a body, the apparatus comprising:
an input stage to receive an electrocardiogram signal from a body connected thereto through a detection electrode input, wherein the input stage is a real-time dynamically adjustable signal transformation stage configured to condition the electrocardiogram signal;
an analysis stage coupled to the input stage to receive the conditioned electrocardiogram signal from the input stage, wherein the analysis stage comprises,
a transformation stage wherein a time domain profile of the conditioned electrocardiogram signal is formed, wherein the time domain profile is a histogram, and
an evaluation stage configured to determine, over the time domain profile, at a plurality of predetermined time intervals, the number of times a spectral time domain dispersion metric (STDM) is in one or more count ranges over the plurality of predetermined time intervals, wherein the count ranges correspond to one or more arrhythmias; and
a classification stage coupled to the evaluation stage to receive the STDM and to determine whether the body is experiencing the arrhythmias.

32. The apparatus of claim 31, wherein the arrhythmias comprises atrial fibrillation, ventricular fibrillation, atrial flutter, or another arrhythmia.

\* \* \* \* \*